United States Patent [19]

Puppel

[11] Patent Number: 4,952,750
[45] Date of Patent: Aug. 28, 1990

[54] PROCESS FOR MAKING P-XYLENE WITH A PURITY OF AT LEAST 99.5%

[75] Inventor: Guenter Puppel, Wulfen, Fed. Rep. of Germany

[73] Assignee: Krupp Koppers GmbH, Essen, Fed. Rep. of Germany

[21] Appl. No.: 339,233

[22] Filed: Apr. 14, 1989

[30] Foreign Application Priority Data

May 5, 1988 [DE] Fed. Rep. of Germany ....... 3815324

[51] Int. Cl.$^5$ .............................................. B01D 9/04
[52] U.S. Cl. .................................... 585/816; 585/817; 62/533; 62/534
[58] Field of Search ............... 585/805, 812, 816, 817; 62/533, 534, 544, 536

[56] References Cited

U.S. PATENT DOCUMENTS

| | | | |
|---|---|---|---|
| 3,410,923 | 11/1968 | Strand et al. | 585/817 |
| 3,435,625 | 4/1969 | Wiegandt | 62/533 X |
| 3,467,724 | 9/1969 | Laurich | 585/817 |
| 3,501,493 | 3/1970 | Oldenburg | 62/534 X |
| 3,541,804 | 11/1970 | Wiegandt et al. | 585/817 |
| 3,643,453 | 2/1972 | Groothuis et al. | 62/536 |
| 3,903,795 | 6/1976 | Wood et al. | 585/816 |

*Primary Examiner*—Glenn Caldarola
*Attorney, Agent, or Firm*—Michael J. Striker

[57] ABSTRACT

This process is an improvement of a process described in German Open Patent Application No. 3703646 for obtaining a p-xylene product with a purity of at least 99.5%. The inert fluid used as a cold carrier is mixed with a crude product starting material, which has a high p-xylene content, in a mixing vessel under rotation to form a resultant mixture. Subsequently the resultant mixture is concentrated to a crystal content of from 30% to 70% and after that the p-xylene crystals are separated in a separator. The purity of the product p-xylene can be increased by heating these crystals in the separator.

13 Claims, 1 Drawing Sheet

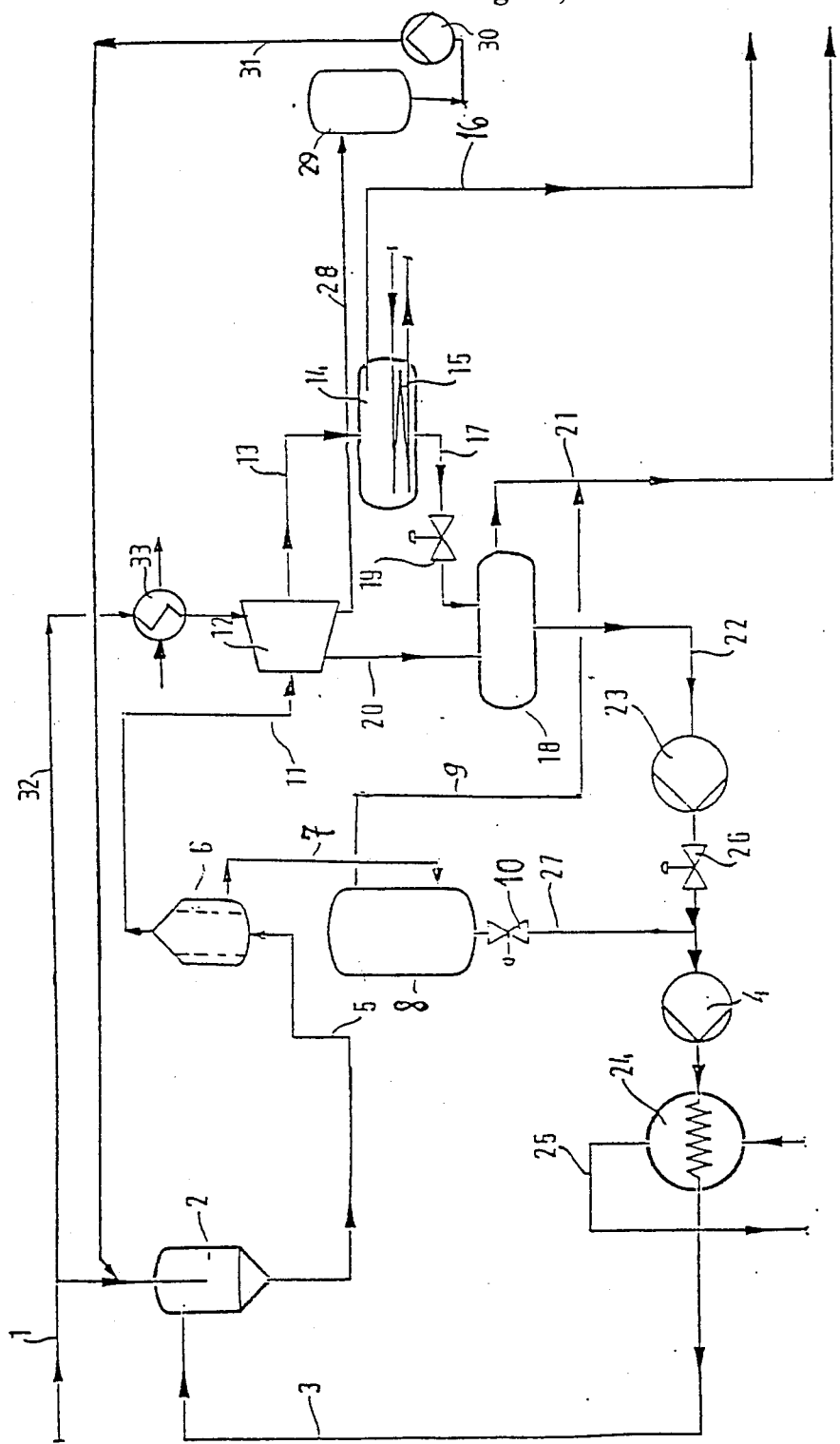

PROCESS FOR MAKING P-XYLENE WITH A PURITY OF AT LEAST 99.5%

BACKGROUND OF THE INVENTION

My invention relates to a process for making high purity p-xylene and, more particularly, for making p-xylene with a purity of at least 99.5 %.

In the German Open Patent Application No. 37 03 646 a process for obtaining p-xylene with at least 99.5 % purity from a crude or initial product is described. In this process the crude product is fed in the fluid state to an inert fluid, advantageously water, whose temperature is under the melting point of pure p-xylene. The crystalline material precipitated by agitation is separated in a separator from the inert fluid and subsequently melted. Residual fluid still present in the melting device is separated from the melted crystals and after that is recovered as p-xylene with the desired purity.

With the help of this process using a crude or initial product made in a production plant already existing a p-xylene with a purity of at least 99.5 % can be produced without the present plant being reconstructed and without stopping its operation.

SUMMARY OF THE INVENTION

It is an object of the present invention to provide an improved process for making p-xylene with at least 99.5 % purity in which process operation is improved or simplified.

It is another object of the present invention to provide an improved process of the above-described kind for making p-xylene with a purity of more than 99.5 %.

It is also an object of our invention to provide a process of the above-described kind using a crude product whose p-xylene content is less than 99 %.

Accordingly these objects and others are attained in a process of the above-described kind according to our invention because the inert fluid used as a cold carrier is fed together with the crude product to a mixing vessel under rotation and the resulting mixture is taken from the bottom portion of the mixing vessel. This mixture is concentrated in a filter unit to form a concentrate until a crystal content of from 30 to 70 % has been reached and subsequently the concentrate is fed directly to a separator.

These steps are simpler than the equivalent steps of the current process because the mixture directly drawn off from the filter unit can be directly fed to the separator and the receiving vessel equipped with a stirring device which was provided for an intermediate step of the current process can be eliminated. Moreover in the process according to our invention the process conditions in the mixing vessel can be improved because the inert fluid is mixed with the crude product by rotation. The funnel or vortex formation because of fluid rotation allows greatly expanded crystal aggregates to be continuously drawn from the mixing vessel. The required rotation can be effected by feeding the inert fluid tangentially into the mixing vessel in which a cooling unit is also provided.

An increase in purity of the p-xylene obtained over the value of 99.5 % can be attained when a concentrate containing the separated p-xylene crystals is heated in the separator to a temperature between 7 and 13° C. so that they leave the separator with a correspondingly increased temperature and are fed to the melting unit. The heating can occur using a suitable fluid, such as preheated water, preheated starting material or another fluid, which may be subsequently easily separated from purified p-xylene. Steam or hot gas, e.g. Nitrogen, can also be used.

In the current process the crude product acting as a starting material has a p-xylene content which is at least 99 %. It has been shown that one can use a crude product with a reduced p-xylene content. Of course in this case the amount of the hydrocarbon mixture, which must be fed back to the process which makes the crude product, increases. On using a crude product with a p-xylene content of about 99 % the amount fed back is about 6 % of the starting material. With the same process conditions the recycled amount with a crude product with 98 % p-xylene increases to about 13 % of the starting material and with a crude product with 97 % p-xylene to about 20 % of the starting material. The operator of the plant making the crude product must decide which course is most profitable.

BRIEF DESCRIPTION OF THE DRAWING

The objects, features and advantages of the present invention will be made more apparent from the following detailed description, reference being made to the accompanying drawing in which:

The sole figure is a flow chart for the process for obtaining p-xylene which is at least 99.5 % pure.

DETAILED DESCRIPTION OF THE INVENTION

The crude product originating in an upstream production unit not shown in the flow chart is conducted by a pipe 1 in the fluid state to the mixing vessel 2. The required inert fluid, whose temperature is under the melting point of the pure p-xylene, is fed to the mixing vessel 2 through the pipe 3 and is fed into it tangentially so that the inert fluid is mixed with the crude product in the mixing vessel 2 under rotation. As an inert fluid in the sense of the invention we mean a fluid in which p-xylene has little or no solubility. Examples of these inert fluids are as follows: water and mixtures of water as well as certain alcohols such as methanol, ethanol and glycol. The temperature of the inert fluid must, as has already been mentioned, be under the melting point of the pure p-xylene, i.e. under 13.26° C., on feeding in the fluid crude product. Advantageously one works with a fluid temperature between 0° and 12° C.

The funnel or vortex formation caused by rotation of the inert fluid in the mixing vessel 2 allows the greatly expanding crystal agqregates to be continuously drawn off from the mixing vessel 2 and to be fed in the pipe 5 from below into the filter unit 6. Here the crystal-fluid mixture is concentrated to a crystal content of 30 to 70 % and subsequently the concentrate so formed is fed directly to the separator 12 over the pipe 11, which is formed as a centrifuge in this case. The separator 12, can, as was mentioned above, be equipped so that it is possible to heat the p-xylene crystals separated from the fluid up to a temperature of from 7° and 13° C. The heated p-xylene crystals are drawn off from the separator 12 and arrive subsequently by the pipe 13 in the melting unit 14, which is provided with the steam-heated heating coil 15. A likely inert fluid residue separates and collects as a heavy phase at the base of the melting unit 14 so that the melted crystals can be drawn off from the upper portion of the melting unit 14 through the pipe 16. It is a matter of a pure product whose p-xylene content is about 99.5 %.

The residue of the inert fluid collecting at the bottom of the melting unit 11 is drawn off through the pipe 17 into the filtrate container 18. A valve 19 is mounted in the pipe 17 so that the fluid withdrawn can be adjusted so that the meniscus between the melted p-xylene and the inert fluid in the melting unit 14 can be kept at constant level. Fluid coming from the separator 12 is conducted into the filtrate container 18. By phase separation the hydrocarbon materials contained in the inert fluid are separated in the filtrate container 18. These separate out as a lighter phase on the fluid surface and can be taken off by the pipe 21. This is a matter of a mixture of o- and m-xylene and ethylbenzene with lower p-xylene content. This mixture can thus be fed back to the process for making the crude product used as the starting material. The amount of the fed back mixture adjusts itself, as was mentioned above, to the purity of the crude product used.

The fluid separated in the filter unit 6 is fed through the pipe 7 into the filter container 8. The accompanying hydrocarbons separate in the filtrate container 8 as a lighter phase on the fluid surface and can be drawn off through the pipe 9 and can be combined with the hydrocarbon material in the pipe 21. Different from the embodiment shown in the flow chart it is also possible to conduct the lighter phase drawn off from the filtrate container 8 over a pipe 9 into the filtrate container 18.

The inert fluid released from the hydrocarbon material is drawn off through the pipe 27 from the filtrate container 8 and is fed with the pump 4 to the heat exchanger 24. The valve 10 thus serves to regulate this run off. The heat exchanger 24 is connected to the cooling circulation loop 25 so that the inert fluid experiences the required cooling in the heat exchanger, before it is fed back by the pipe 3 to the mixing vessel 2.

The pipe 22 coming from the filtrate container 18 opens into the pipe 27. Inert fluid released from the hydrocarbon material collected at the bottom of the filtrate container 18 is drawn off through these pipes and is fed back by the pump 23 to the pipe 27. The valve 26 acts for regulation of the fluid flow. In a way which differs from the embodiment shown this feed back can also occur into the filtrate container 8.

In case of a partial flow of the crude product to be used for heating of the p-Xylene crystals in the separator 12, this partial flow is taken off from the flow in pipe 1 through the pipe 32. When using a crude product with a p-Xylene content of about 99 % this partial flow can be about 25 % of the starting material. The partial flow drawn off through the pipe 32 experiences the required heating in the heat exchanger 33 and reaches after that the separator 12. The fluid filtrate accumulating on heating the p-xylene crystals is taken off separately in this case through the pipe 28 from the separator 12 and arrives in the pump reservoir 29. From these it is fed back with the pump 30 over the pipe 31 to the pipe 1 and added to the starting material.

A crystal deposit on cooling down of the inert fluid circulated in the heat exchanger 24 can be avoided because the fluid in the pipes 22 and 27 can be mixed in a p-xylene mixture with a reduced p-xylene content so that the p-xylene content of the xylenes dissolved in the fluid is reduced so far that the start of crystallization occurs at a temperature below the outlet temperature of the cooled inert fluid from the heat exchanger.

An emulsion formed, as can arise for example in the separator 12 or the pump, is encountered by the structures of customary devices for breaking up emulsions in the connected pipes.

Subsequently the operation of the process according to our invention is illustrated with the embodiment presented:

A crude product with a p-xylene content of 99 % is used. This crude starting material or initial product was conducted to the mixing vessel 2 with a temperature of 30° C. Water was used as an inert fluid, which was fed tangentially into the mixing vessel, which was equipped with a stirring device, at a temperature of about 2° C. The water-crystal mixture drawn from the mixing vessel 2 has a crystal content of 7 to 8 % and was dewatered in the filter unit 6 until the crystal content was about 30 %. This crystal slurry was fed continuously to a centrifuge at a temperature of about 6° C., which functions in this case as a separator 12. Without additional heat of the p-xylene deposited there a final product with a p-xylene content of 99.5 % purity was attained.

An additional increase in purity of the accumulating final product can be attained when a partial flow of the starting crude product of about 25 % was fed to the centrifuge for heating the p-xylene crystals. This partial flow was conducted into the centrifuge at a temperature of about 45° C. The purity of the accumulating final product can be increased because of that to over 99.8 % p-xylene.

While the invention has been illustrated and described as embodied in a process for obtaining high purity p-xylene, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims:

1. In a process for obtaining p-xylene with a purity of at least 99.5 % from a crude product with a high p-xylene content comprising conducting said crude product in a fluid state into an inert fluid whose temperature is under the melting point of pure p-xylene, separating a crystalline phase precipitated from said inert fluid in a separator under stirring, then melting said crystalline phase to form a melted crystalline phase, separating residual portions of said inert fluid accompanying said melted crystalline phase from said melted crystalline phase and after that drawing off said p-xylene with a predetermined level of said purity, the improvement comprising mixing said inert fluid under rotation with said crude product in a mixing vessel to form a resultant mixture, drawing off said resultant mixture from a bottom portion of said mixing vessel, concentrating said resultant mixture to a crystal content of from 30 to 70 % to form a concentrate and subsequently feed said concentrate directly to said separator. wherein during said separating said crystalline phase in said separator heating said concentrate containing said p-xylene in said separator to a temperature between 7 and 13° C. to obtain said p-xylene with said purity of more than 99.5%

2. The improvement defined in claim 1 further comprising heating said concentrate in said separator with preheated water.

3. The improvement defined in claim 1 further comprising heating said concentrate in said separator with preheated crude product.

4. The improvement defined in claim 1 further comprising heating said concentrate in said separator with steam.

5. The improvement defined in claim 1 further comprising heating said concentrate in said separator with another fluid which may be easily separated from said p-xylene.

6. The improvement defined in claim 1 further comprising heating said concentrate in said separator with a heated gas.

7. The improvement defined in claim 6 wherein said heated gas is nitrogen.

8. The improvement defined in claim 1 further comprising increasing the amount of a hydrocarbon mixture fed back for production of said crude product when using a portion of said crude product whose content of said p-xylene is less than 99 %.

9. The improvement defined in claim 1 in which said inert fluid comprises water.

10. A process for obtaining p-xylene with a purity of at least 99.5 % from a crude product with a high p-xylene content comprising the steps of:
  a. mixing said crude product with an inert fluid in a mixing vessel under rotation to form a resultant mixture;
  b. drawing off said resultant mixture from a bottom portion of said mixing vessel;
  c. concentrating said resultant mixture to a crystal content of from 30 to 70 % to form a concentrate;
  d. separating a crystalline phase precipitated from said concentrate in a separator under stirring;
  e. during said separating heating said concentrate containing said p-xylene in said separator to a temperature between 7 and 13° C.;
  f. then after said separating melting said crystalline phase to form a melted crystalline phase;
  g. separating residual portions of said inert fluid from said melted crystalline phase; and after that
  h. drawing off said p-xylene with a predetermined level of said purity.

11. A process according to claim 10, wherein said inert fluid is water and said heating of said concentrate is performed with preheated water.

12. The improvement defined in claim 10 in which said inert fluid comprises water.

13. The improvement defined in claim 10 in which said heating of said concentrate is performed with a heated gas.

* * * * *